United States Patent [19]

Hornung et al.

[11] Patent Number: 5,776,363
[45] Date of Patent: Jul. 7, 1998

[54] COMPOUNDS HAVING SIDE CHAINS WITH MULTIPLE METHYL BRANCHES AND THEIR USE IN LIQUID-CRYSTAL MIXTURES

[75] Inventors: Barbara Hornung, Hasselroth; Rainer Wingen, Hattersheim; Michael Morr, Wolfenbüttel; Detlef Lötzsch; Gerd Heppke, both of Berlin, all of Germany

[73] Assignee: Hoechst Aktiengesellschaft, Frankfurt, Germany

[21] Appl. No.: 683,298

[22] Filed: Jul. 18, 1996

[30] Foreign Application Priority Data

Jul. 21, 1995 [DE] Germany ............ 195 26 611.0

[51] Int. Cl.$^6$ .............. C09K 19/52; C07D 239/00; C07D 285/08; C07D 319/06
[52] U.S. Cl. ............ 252/299.01; 252/299.61; 252/299.62; 252/299.63; 544/242; 544/336; 548/128; 548/136; 549/369; 546/184; 546/269.1
[58] Field of Search ............ 252/299.01, 299.61, 252/299.63, 299.64, 299.65, 299.66, 299.67; 544/242, 298, 336, 358; 546/184, 269.1; 549/369, 1; 548/128, 129, 130, 136, 146

[56] References Cited

U.S. PATENT DOCUMENTS 5,250,222  10/1993  Kelly et al. .............. 252/299.66
5,356,564  10/1994  Tsai et al. .............. 252/299.64

FOREIGN PATENT DOCUMENTS 0191860   8/1986  European Pat. Off.
WO 86/00087  1/1986  WIPO Primary Examiner—Shean C. Wu
Attorney, Agent, or Firm—Frommer Lawrence & Haug LLP

[57] ABSTRACT

Compounds of the formula (I) having side chains with multiple methyl branches $$R^1(-A^1-M^1)_a(-A^2-M^2)_b(-A^3-M^3)_c(-A^4)-G(-C_*H(CH_3)-CH_2)_n-R^2 \quad (I)$$

where
* is a chiral carbon atom;
$A^1$, $A^2$, $A^3$, $A^4$ are, for example, 1,4-phenylene, pyrimidine-2,5-diyl or 1,3,4-thiadiazole-2,5-diyl;
$M^1$, $M^2$, $M^3$, $M^4$ are, for example, —CO—O— or —O—CO—;
G is, for example, —CO—O—CH$_2$, —O—CH$_2$— or —O—;
$R^2$ is, for example, methyl or ethyl;
a, b and c are 0 or 1 and a+b+c is 1, 2 or 3; and
n is preferably 3 or 4,
are suitable as components, in particular dopes, for liquid-crystalline mixtures and methods of using these compounds in liquid-crystal mixtures.

9 Claims, No Drawings

5,776,363

COMPOUNDS HAVING SIDE CHAINS WITH MULTIPLE METHYL BRANCHES AND THEIR USE IN LIQUID-CRYSTAL MIXTURES

RELATED APPLICATION

This application claims priority to German application No. 19526611.0, filed Jul. 21, 1995, incorporated herein by reference.

BACKGROUND OF THE INVENTION

1. Field of the Invention

This invention relates to compounds having side chains with multiple methyl branches and the use thereof in liquid-crystal mixtures.

2. Description of the Related Art

The following references and those referred to hereinafter, each of which are hereby incorporated by reference, disclose the state of the art.

In addition to nematic and cholesteric liquid crystals, optically active tilted smectic (ferroelectric) liquid crystals have also been used recently in commercial display devices.

Clark and Lagerwall showed that the use of ferroelectric liquid crystals (FLCs) in very thin cells results in optoelectrical switching or display elements which have faster response times by a factor of up to 1000 when compared with conventional TN ("twisted nematic") cells (see, for example, EP-A 0 032 362). On the basis of this and other favorable properties, such as the possibility of bistable switching and the virtually viewing angle-independent contrast, FLCs are fundamentally highly suitable for areas of application such as computer displays.

For the use of FLCs in electro-optical or fully optical components, certain compounds are required. In particular, compounds which form tilted or orthogonal smectic phases and are themselves optically active are required. Alternatively, compounds in which ferroelectric smectic phases can be induced by doping. While these compounds form smectic phases, they are not themselves optically active. The doping is with optically active compounds. The desired phase is desirably stable over the broadest possible temperature range.

In order to achieve good contrast in electro-optical components, a uniform planar alignment of the liquid crystals is necessary. Good alignment in the $S_A$ and $S^*_C$ phase can be achieved, for example, if the phase sequence of the liquid-crystal mixture is, with decreasing temperature:

isotropic→N*→$S_A$→$S^*_C$

The prerequisite is that the pitch of the helix in the N* phase is very large (greater than 10 μm) or, preferably fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid. pp. 344–347). This is achieved by adding one or more optically active dopes which induce a right-hand helix to the chiral liquid-crystal mixture which has, for example, a left-hand helix in the N* phase, in such amounts that the helix is compensated.

An additional prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213–134 and 114 (1984), 151–187). As in the case of the cholesteric pitch, this is achieved by using dopes having the opposite rotation of the helix.

The optical response time τ |μs| of ferroelectric liquid-crystal systems, which should be as short as possible, depends on the rotational viscosity of the system γ|mPas|, the spontaneous polarization $P_s$|nC/cm²| and the electric field strength E|V/m|, in accordance with the equation $$\tau \sim \frac{\gamma}{P_S \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably≈0.13, and a low positive or preferably negative dielectric anisotropy Δε are required (see, for example, S. T. Lagerwall et al., "Ferroelectric Liquid Crystals for Displays", SID Symposium, Oct. Meeting 1985, San Diego, Calif., USA).

The totality of these requirements can only be achieved by means of mixtures comprising a plurality of components. The base (or matrix) used preferably comprises compounds which if possible themselves already have the desired phase sequence I→N→$S_A$→$S_C$. Further components of the mixture are frequently added in order to lower the melting point and to broaden the $S_C$ and usually also the N phase, to induce optical activity, for pitch compensation and to match the optical and dielectric anisotropy; however, the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP-A 0 405 346. In contrast to the SSFLCD effect, utilization of these effects requires a liquid-crystalline material having a short $S_C$ pitch.

Optically active compounds having a methyl branch in the side chain are described, for example, in WO-A 86/0087.

However, since the development of ferroelectric liquid-crystal mixtures in particular can in no way be regarded as complete, the manufacturers of displays are still interested in a very wide variety of components, in particular dopes, for mixtures. Another reason for this is that only the interaction of the liquid-crystalline mixtures with the individual components of the display device or of the cells (for example the alignment layer) allows conclusions to be drawn on the quality of the liquid-crystalline mixtures too.

OBJECT OF THE INVENTION

The object of the present invention was therefore to provide novel compounds which are suitable in liquid-crystalline mixtures for improving the property profile of these mixtures.

SUMMARY OF THE INVENTION

It has now been found that compounds with multiple methyl branches are particularly suitable for use in liquid-crystal mixtures.

DETAILED DESCRIPTION OF THE INVENTION

The invention therefore relates to compounds of the formula (I) with multiple methyl branches

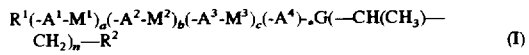  (I)

in which the symbols and indices have the following meanings:

* is a chiral carbon atom;

$R^1$ is hydrogen, —CN, —F, —Cl, —CF$_3$, —CHF$_2$, —CH$_2$F, —OCF$_3$, —OCHF$_2$, —OCH$_2$F or a straight-chain or branched alkyl radical having 1 to 20 carbon atoms (with or without an asymmetrical carbon atom), where one or more —CH$_2$— groups may also be replaced by —O—, —S—, —CO—O—, —O—CO—, —O—CO—O—, —CO—, —CS—, —CH=CH—, —C≡C—, cyclopropane-1,2-diyl, —Si(CH$_3$)$_2$—, 1,4-phenylene, trans-1,4-cyclohexylene or trans-1,3-cyclopentylene, with the proviso that oxygen atoms and/or sulfur atoms must not be bonded directly to one another, and/or where one or more H atoms of the alkyl radical may be substituted by —F, —Cl, —Br, —OR$^3$, —SCN, —OCN or —N$_3$, or $R^1$ is alternatively one of the following groups (optically active or racemic):

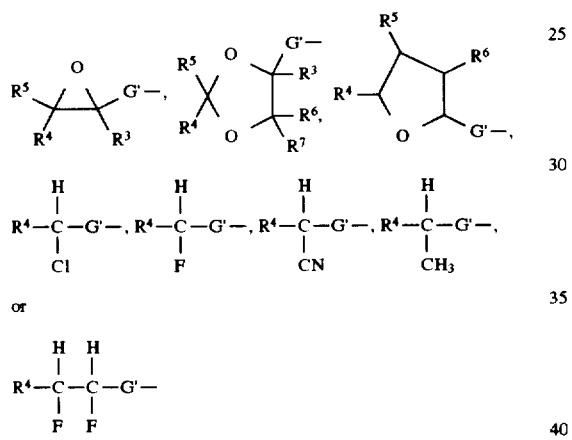

or $R^1$ is a radical of the formula -G-(C$_*$H(CH$_3$)—CH$_2$)$_n$R$^2$, which is preferably identical with the radical on the other side of the molecule;

$R^2$ is an n-alkyl group having 1 to 6 carbon atoms, preferably methyl or ethyl;

G is —CO—O—CH$_2$—, —CO—O—, —O—CO—, —O—CO—O—CH$_2$—, —O—CO—O—, —OCH$_2$—, —O—, —S— or a single bond;

G' is —CO—O—, —CH$_2$—O— or a single bond;

$R^3$, $R^4$, $R^5$, $R^6$ and $R^7$ are identical or different and are hydrogen or a straight-chain or branched alkyl radical having 1 to 16 carbon atoms (with or without an asymmetrical carbon atom), where one or more —CH$_2$— groups may also be replaced by —O— and/or —CH=CH—, with the proviso that oxygen atoms must not be bonded directly to one another, and/or where one or more H atoms of the alkyl radical may be substituted by —F or —Cl; $R^4$ and $R^5$ together may also be —(CH$_2$)$_4$— or —(CH$_2$)$_5$— if they are bonded to an oxirane, dioxolane or tetrahydrofuran system;

$M^1$, $M^2$, $M^3$ and $M^4$ are identical or different and are —CO—O—, —O—CO—, —O—CO—O—, —CH$_2$—O—, —O—CH$_2$—, —CH$_2$—S—, —S—CH$_2$—, —CH=CH— or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH$_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, or naphthalene-2,6-diyl, in which one or more H atoms may be replaced by F, Cl and/or CN;

a, b and c are 0 or 1 and a+b+c is 1, 2 or 3; and n is 2, 3, 4, 5 or 6, preferably 3 or 4, in particular 4.

Preference is given to optically active compounds of the formula (I).

Preference is also given to compounds of the formula (I) in which the symbols and indices have the following meanings:

$R^1$ is hydrogen, or a straight-chain or branched alkyl radical having 1 to 20 carbon atoms (with or without an asymmetrical carbon atom), where one or more CH$_2$— groups may also be replaced by —O—, —CO—O—, —O—CO—, —O—CO—O—, —CH=CH—, —C≡C—, cyclopropane-1,2-diyl or —Si(CH$_3$)$_2$—, with the proviso that oxygen atoms must not be bonded directly to one another, and/or where one or more H atoms of the alkyl radical may be substituted by —F or —Cl, or $R^1$ is one of the following groups (optically active or racemic):

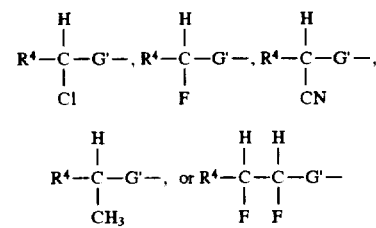

or $R^1$ is a group of formula -G-(C$_*$H(CH$_3$)—CH$_2$)$_n$—R$^2$;

$R^2$ is methyl or ethyl;

G is —CO—O—CH$_2$—, —CO—O—, —O—CO—, —O—CO—O—CH$_2$—, —O—CO—O—, —O—CH$_2$—, —O— or a single bond;

G' is —CO—O—, —CH$_2$—O— or a single bond;

$R^4$ is hydrogen or a straight-chain or branched alkyl radical having 1 to 16 carbon atoms (with or without an asymmetrical carbon atom), where one or more —CH$_2$— groups may also be replaced by —O—, with the proviso that oxygen atoms must not be bonded directly to one another, and/or where one or more H atoms of the alkyl radical may be substituted by —F;

$M^1$, $M^2$, $M^3$ and $M^4$ are identical or different and are —CO—O—, —O—CO—, —O—CO—O— —CH$_2$—O—, —O—CH$_2$—, —C≡C—, —CH$_2$—CH$_2$—CO—O—, —O—CO—CH$_2$—CH$_2$— or a single bond;

A¹, A², A³ and A⁴ are identical or different and are 1,4-phenylene, in which one or more H atoms may be replaced by F, Cl and/or CN, pyrazine-2,5-diyl, in which one or two H atoms may be replaced by F, pyridazine-3,6-diyl, in which one or two H atoms may be replaced by F, pyridine-2,5-diyl, in which one or more H atoms may be replaced by F, pyrimidine-2,5-diyl, in which one or two H atoms may be replaced by F, trans-1,4-cyclohexylene, in which one or two H atoms may be replaced by CN and/or $CH_3$, 1,3,4-thiadiazole-2,5-diyl, 1,3-thiazole-2,4-diyl, in which one H atom may be replaced by F, 1,3-thiazole-2,5-diyl, in which one H atom may be replaced by F, thiophene-2,5-diyl, in which one H atom may be replaced by F, or naphthalene-2,6-diyl, in which one or more H atoms may be replaced by F;

a, b and c are 0 or 1 and a+b+c is 1, 2 or 3; and n is 3 or 4.

Particular preference is given to compounds of the formula (I) in which the symbols and indices have the following meanings:

$R^1$ is hydrogen, or a straight-chain or branched alkyl radical having 1 to 20 carbon atoms (with or without an asymmetrical carbon atom), where one or two $CH_2$— groups may also be replaced by —O—, —CO—O—, —O—CO—, —C≡C—, cyclopropane-1,2-diyl or —Si(CH₃)₂—, with the proviso that oxygen atoms must not be bonded directly to one another, and/or where one or more H atoms of the alkyl radical may be substituted by —F, or $R^1$ is a group of the formula -G-(C*H(CH₃)—CH₂)ₙ—R²;

$R^2$ is methyl or ethyl;

G is —CO—O—CH₂—, —CO—O—, —O—CO—, —O—CH₂—, —O— or a single bond;

M¹, M², M³ and M⁴, are identical or different and are —CO—O—, —O—CO—, —CH₂—O—, —O—CH₂—, or a single bond;

A¹, A², A³ and A⁴ are identical or different and are 1,4-phenylene, in which one or more H atoms may be replaced by F, pyridine-2,5-diyl, in which one H atom may be replaced by F, pyrimidine-2,5-diyl, trans-1,4-cyclohexylene, 1,3,4-thiadiazole-2,5-diyl, 1,3-thiazole-2,4-diyl, 1,3-thiazole-2,5-diyl or naphthalene-2,6-diyl;

a, b and c are 0 or 1 and a+b+c is 1, 2 or 3; and n is 3 or 4.

Very particular preference is given to compounds of the formula (I) in which the symbols and indices have the following meanings:

$R^1$ is a straight-chain or branched alkyl, alkoxy or ester group having 1 to 16 carbon atoms;

$R^2$ is methyl or ethyl;

G is —CO—O—CH₂—, —CO—O—, —O—CO—, —O—CH₂— or —O—;

M¹, M², M³ and M⁴, are identical or different and are —CO—O—, —O—CO—, —CH₂—O—, —O—CH₂—, or a single bond;

A¹, A², A³ and A⁴ are identical or different and are 1,4-phenylene, in which one or two H atoms may be replaced by F, pyrimidine-2,5-diyl, pyridine-2,5-diyl, in which one H atom may be replaced by F, trans-1,4-cyclohexylene, 1,3,4-thiadiazole-2,5-diyl or 1,3-thiazole-2,5-diyl;

a, b and c are 0 or 1 and a+b+c is 1, 2 or 3; and n is 3 or 4.

Special preference is given to compounds of the formula (I) in which the group (-A¹-M¹)ₐ(-A²-M²)ᵦ(-A³-M³)𝒸(-A⁴) has one of the following meanings:

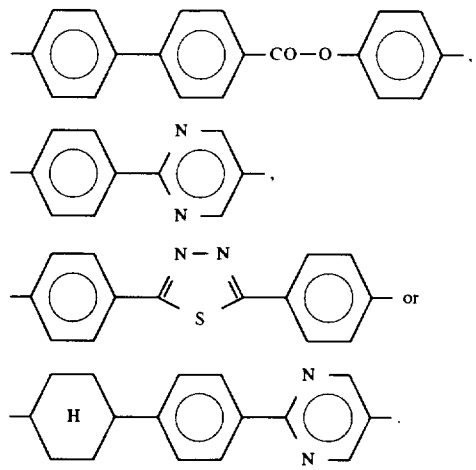

Formula (I) covers compounds which can exist in various absolute configurations. For example, for compounds where n=4, substances in the (R,R,R,R), (R,R,R,S), (R,R,S,R), (R,S,R,R), (S,R,R,R), (S,S,R,R), (S,R,S,R), (S,R,R,S), (R,S,R,S), (R,S,S,R), (R,R,S,S), (S,S,S,R), (S,S,R,S), (S,R,S,S), (R,S,S,S) and (S,S,S,S) configuration are covered.

The compounds are preferably in the (R,R,R,R) or (R,R,R) configuration.

The novel compounds are prepared by methods known per se from the literature, as described in the standard works of organic chemistry, for example Houben-Weyl, Methoden der Organischen Chemie [Methods of Organic Chemistry], Georg-Thieme-Verlag, Stuttgart.

The preparation is carried out under reaction conditions which are known and are suitable for said reactions. Use can also be made here of variants which are known per se, but are not described here in greater detail.

If desired, the starting materials can also be formed in situ by not isolating them from the reaction mixture, but instead immediately converting them further into the compounds of the formula (I).

The synthesis of the radical R¹(-A¹-M¹)ₐ(-A²-M²)ᵦ(-A³-M³)𝒸(-A) or a suitable precursor thereof, protected if desired, is carried out by methods known per se and customary to the person skilled in the art.

The preparation is carried out under reaction conditions which are known and suitable for said reactions. Use may also be made here of variants which are known per se, but are not described here in greater detail.

For example, reference may be made to DE-A 23 44 732, 24 50 088, 24 29 093, 25 02 94, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 0 391 203 for compounds containing pyridine-2,5-diyl groups; DE-A 32 31 462 for compounds containing pyridazine-3,6-diyl groups; EP-A 309 514 for compounds containing 1,3,4-thiadiazole-2,5-diyl, 1,3-thiazole-2,4-diyl and 1,3-thiazole-2,5-diyl groups; WO-A 92/16500 for naphthalene-2,6-diyl groups; DE-A 37 10 890 for bicyclo [2.2.2]octane-1,4-diyl groups; K. Seto et al., Journal of the Chemical Society, Chemical Communications 1988, 56, for dioxoborinane-2,5-diyl groups.

The preparation of disubstituted pyridines, disubstituted pyrazines, disubstituted pyrimidines and disubstituted pyridazines is also given, for example, in the orresponding volumes in the series "The Chemistry of Heterocyclic Compounds" by A. Weissberger and E. C. Taylor (Editors).

Dioxane derivatives are expediently prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures between about 20° C. and about 150° C., preferably between 80° C. and 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitriles or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group by a fluorine atom, for example by the methods of Balz and Schiemann (see e.g. R. Bartsch et al., J. Am. Chem. Soc. 98 (1976) 6753).

As far as the linking of ring systems to one another is concerned, reference may be made, for example to: N. Miyaura, T. Yanagai and A. Suzuki in Synthetic Communications 11 (1981), 513–519; DE-C-39 30 663; M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 for the direct linking of aromatics and heteroaromatics; DE-A 32 01 721 for compounds containing —$CH_2CH_2$— bridges, and Koji Seto et al. in Liquid Crystals 8 (1990) 861–870 for compounds containing —C≡C— bridges.

Esters of the formula (I) can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known and can be prepared analogously to known processes.

Particularly suitable reactive derivatives of said carboxylic acids are the acid halides, especially the chlorides and bromides, furthermore the anhydrides, for example also mixed anhydrides, azides or esters, in particular alkyl esters having 1 to 4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This can then be reacted with the corresponding alkyl halide, alkyl sulfonate or dialkyl sulfate, expediently in an inert solvent, such as acetone, 1,2-dimethoxyethane, DMF or dimethylsulfoxide, or alternatively with an excess of aqueous or aqueous/alcoholic NaOH or KOH at temperatures between about 20° and 100° C.

Regarding the synthesis of specific radicals $R^1$, reference may additionally be made, for example, to EP-A 0 355 008 for compounds containing silicon-containing side chains and to EP-A 0 292 954 and EP-A 0 398 155 for compounds containing cyclopropyl groups in the side chain.

The radical G(—$C_nHCH_3$—$CH_2$)$_n R^2$ where n=3 or 4 can expediently be prepared via the methyl ester of 2,4,6,8-tetramethyldecanoic, 2,4,6,8-tetramethylundecanoic or 2,4,6-trimethyloctanoic acid.

The compounds can, in the form of the R,R,R- or R,R,R,R-isomers, be obtained in a simple manner and in large amounts from the preen gland of domestic geese or of the Muscovy duck, *Cairina moschata*, as shown in

Scheme 1

Goose tails
125 kg

Cutting out by hand

Preen glands
16–17 kg

1) Comminution using Ultraturrax
    2) Extraction with ethyl acetate
    3) Filtration through kieselguhr Crude wax + solids
2 kg (with about 1.25 kg of 1 + 2)

1) Transesterification    Column
    using 5% HCl in MeOH  chromatography
    2) Distillation Methyl oleate Fraction 1 +    Fraction 2
octadecanol (1a)    Triglycerides
(1b) + (1c) 0.6 kg    80% of triolein Split tube distillation
Methyl 2,4,6,8-tetra-  Methyl 2,4,6,8-tetra-
methyldecanoate    methylyundecanoate
(1b) 380 g    (1c) 40 g $$\text{structure (1)} \quad \text{COOMe}$$

| 1 | a | b | c |
|---|---|---|---|
| n | 0 | 1 | 1 |
| m | 0 | 0 | 1 |

The process is described in M. Morr, V. Wray, J. Fortkamp and R. D. Schmidt, Liebigs Ann. Chem. 1992, p. 433.

The methyl esters (1) can be esterified directly with an appropriately substituted or protected fragment RG-($A^4$)-($M^3$-$A^3$)$_c$(-$M^2$-$A^2$)$_b$(-$M^1$-$A^1$)$_a$-$R^1$ to give compounds of the formula (I).

RG here is a reactive group, for example halogen, alkali metal, metal-halogen, —O-metal, OH or CO-halogen, which enables linking of the fragment with multiple methyl branches, for example by reaction with the compounds (1).

However, the methyl esters (1) can also, as shown, for example, in Scheme 2, be converted into the alcohols (2) or (3), which can then in turn be etherified or esterified using suitably substituted or protected fragments RG-($A^4$)$_d$-($M^3$-$A^3$)$_c$(-$M^2$-$A^2$)$_b$(-$M^1$-$A^1$)$_a$-$R^1$ to give compounds of the formula (I).

Scheme 2

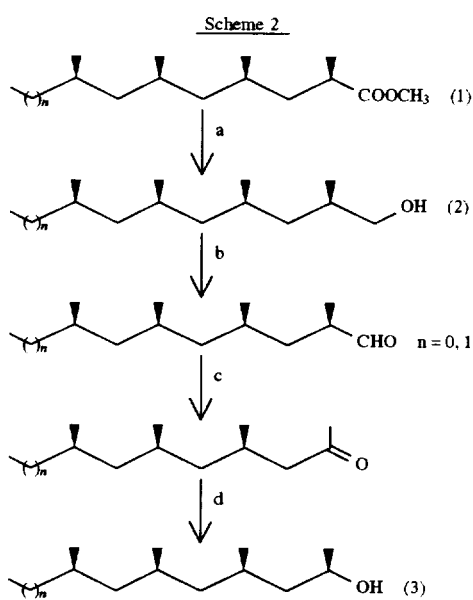

(a) LiAlH$_4$; (b) pyridinium chlorochromate (PCC), CH$_2$Cl$_2$; (c) 1,4-diazabicyclo[2.2.2]octane (DABCO), 2,2'-piperidyl-Cu complex, t-BuOH, air; (d) (S)-methyloxazaborolidine, TH$_3$/BH$_3$, THF, followed by column chromatography on silica gel using CH$_2$Cl$_2$/diisopropyl ether 9:1 as eluent.

The alcohols (2) and (3) can also be converted by standard methods into halides, which then allow direct bonding to the fragment $(A^4)_d-(M^3-A^3)_c(-M^2-A^2)_b(-M^1-A^1)_a-R^1$, for example by Grignard or other organometallic reactions.

The preparation of intermediates, such as the alcohol (3), can of course also be effected by stereoselective synthesis. This is particularly advantageous if isomers other than the (2R,4R,6R,8R)-isomer are to be prepared.

By way of example, two synthesis sequences of this type are illustrated in Schemes 3 and 4.

Scheme 3

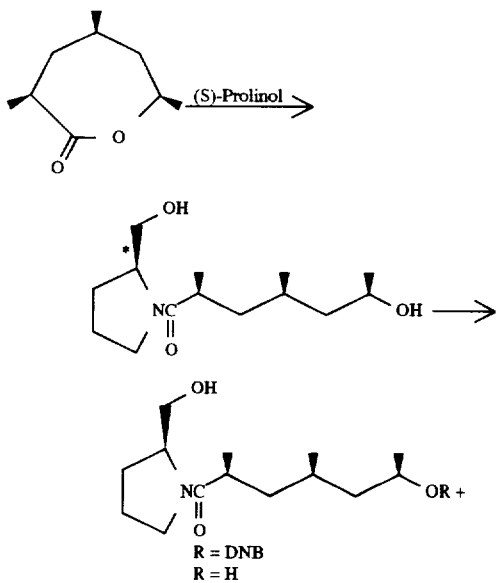

Scheme 3 -continued

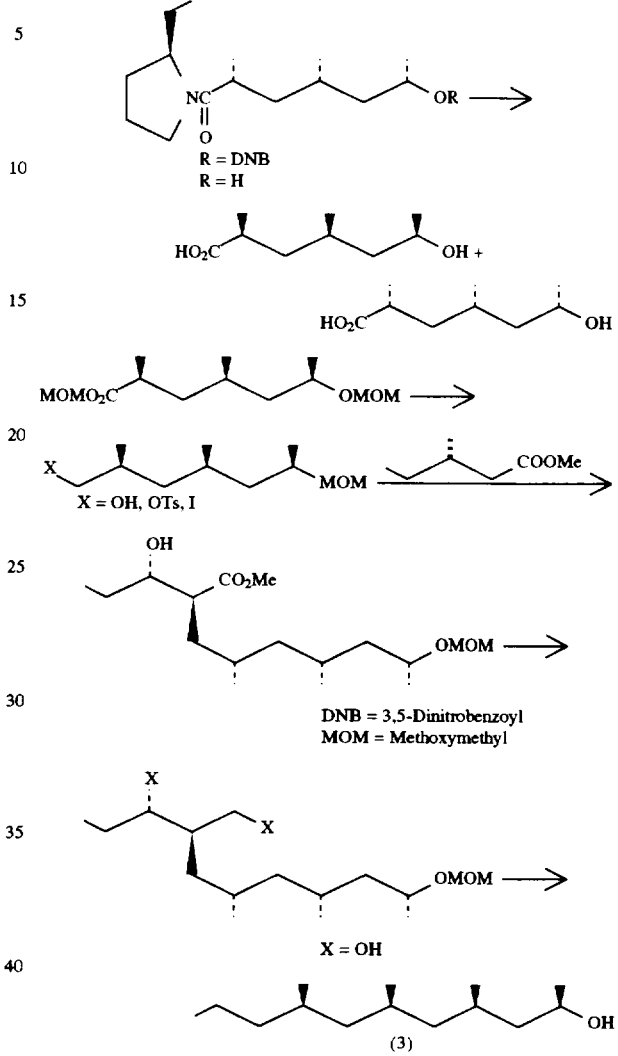

DNB = 3,5-Dinitrobenzoyl
MOM = Methoxymethyl

K. Mori et al., Tetrahydron 1986, 42, 5539.

Scheme 4

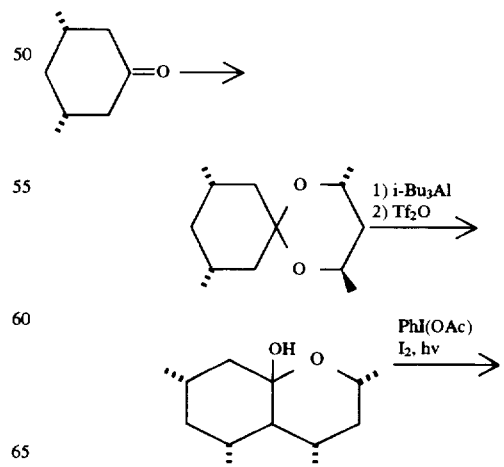

-continued
Scheme 4

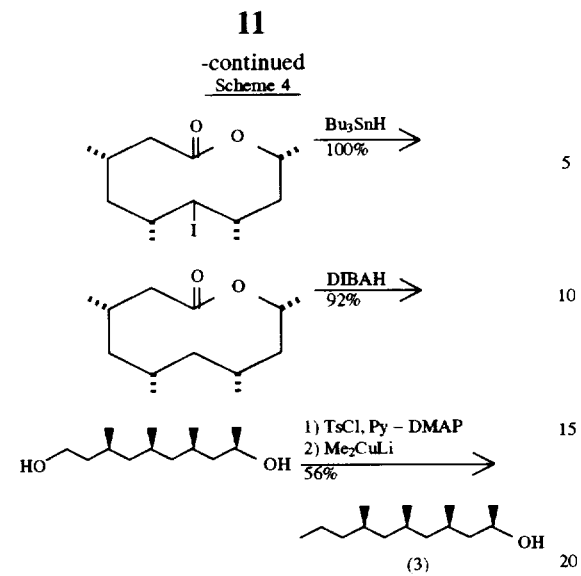

Tf$_2$O = trifluoroacetic anhydride

DIBAH = diisobutylammonium hydride

DMAP = 4-(dimethylammino)pyridine

H. Yamamoto et al., J. Org. Chem. 1990, 55, 5814.

The provision of compounds of the formula (I) very generally considerably broadens the range of liquid-crystalline substances which are suitable. from various application points of view, for the preparation of liquid-crystalline mixtures.

In this connection, the compounds of the formula (I) have a broad range of applications. They can be used as optically active dopes. Depending on the choice of substituents, compounds of the formula (I) can also be used as liquid-crystalline base materials, or they can be added to liquid-crystalline base materials from other classes of compound, in order, for example, to modify the dielectric and/or optical anisotropy of a dielectric of this type and/or to optimize its threshold voltage and/or its viscosity.

In particular, $P_s$ and the tilt angle can be improved.

The invention also relates to the use of compounds of the formula (I) in liquid-crystal mixtures, preferably ferroelectric, antiferroelectric and nematic mixtures, in particular ferroelectric mixtures.

The invention furthermore relates to liquid-crystal mixtures, preferably ferroelectric, antiferroelectric and nematic mixtures, in particular ferroelectric mixtures, containing one or more compounds of the formula (I).

The liquid-crystal mixtures according to the invention generally contain from 2 to 35, preferably from 2 to 25, more preferably from 2 to 20 components.

They generally contain from 0.01 to 80% by weight, preferably from 0.1 to 60% by weight, more preferably from 0.1 to 30% by weight, of one or more, preferably 1 to 5, more preferably 1 to 3, most preferred 1, of the compounds of the formula (I) according to the invention.

Further components of liquid-crystal mixtures containing compounds of the formula (I) according to the invention are preferably selected from known compounds having smectic and/or nematic and/or cholesteric phases. These include, for example:

derivatives of phenylpyrimidine, as described, for example, in WO 86/06401 and U.S. Pat. No. 4,874,542, meta-substituted aromatic compounds having a six-membered ring, as described, for example, in EP-A 0 578 054, silicon compounds, as described, for example, in EP-A 0 355 008, mesogenic compounds containing only one side chain as described, for example, in EP-A 0 541 081, hydroquinone derivatives, as described, for example, in EP-A 0 603 786, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, and thiadiazoles and thiazoles, as described, for example, in EP-A 0 309 514.

Examples of suitable chiral, non-racemic dopes are:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, optically active tetrahydrofuran-2-carboxylic esters, as described, for example, in EP-A 0 355 561, and optically active 2-fluoroalkyl ethers, as described, for example, in EP-A 0 237 007 and U.S. Pat. No. 5,051,506.

The mixtures can in turn be used in electro-optical or fully optical elements, for example display elements, switching elements, light modulators, elements for image processing and/or signal processing or generally in the area of nonlinear optics.

Liquid-crystalline mixtures containing compounds of the formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1987).

The mixtures are furthermore suitable for field treatment, i.e. for operation in the quasi-bookshelf geometry (QBG) (see, for example, H. Rieger et al., SID 91 Digest (Anaheim), 1991, p. 396).

The novel mixtures are likewise suitable for use in ferroelectric liquid-crystal displays which are based on utilization of the DHF effect or the PSFLCD effect (pitch stabilized ferroelectric liquid-crystal display, also known as SBF, short pitch bistable ferroelectric effect).

In addition, the compounds of the formula (I) can also be used as components of antiferroelectric liquid-crystal mixtures.

The invention is described in greater detail by means of the examples, but this is not intended to represent a limitation.

EXAMPLES

Example 1

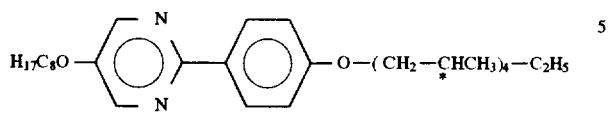

0.55 g (2.09 mmol) of triphenylphosphine is dissolved in THF. 0.36 g (2.09 mmol) of diethyl azodicarboxylate (DEAD) is added dropwise at 0° C., and the mixture is stirred for a further ½ hour without cooling. 0.30 g (1.39 mmol) of (2R,4R,6R,8R)-2,4,6,8-tetramethyldecanol and 0.42 g (1.39 mmol) of 2-(4-hydroxyphenyl)-5-octyl-oxypyrimidine are added. The mixture is stirred at room temperature for 5 hours, the sulfur distilled off, and the residue is chromatographed on silica gel using $CH_2Cl_2$ as eluent.

Yield: 0.16 g., m.p.: 46° C., $|\alpha|_D^{20}$ (2% in $CHCl_3$): −1.25°.

Example 2

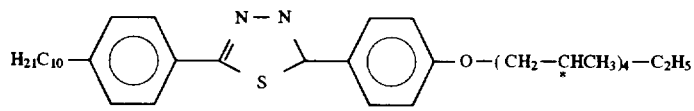

0.36g (2.09 mmol) of DEAD is added dropwise at 0° C. to a solution of 0.55 g (2.09 mmol) of triphenylphosphine in 50 ml of THF, and the mixture is stirred for a further 1 hour without cooling. 0.30 g (1.39 mmol) of (2R,4R,6R,8R)-2, 4,6,8-tetramethyldecanol and 0.55 g (1.39 mmol) of 2-(4-hydroxyphenyl)-5-(4-decylphenyl)-1,3,4-thiadiazole are added, and the mixture is stirred at room temperature for 5 hours, the solvent is distilled off and the residue is purified by chromatography on silica gel using $CH_2Cl_2$ as eluent. Yield: 0.17 g.

X 64 ($S_C^*$ 59) I. $P_S$ (55.5° C.): 8.6 nCcm$^{-2}$ $|\alpha|_D^{20}$ (2% in $CHCl_3$): −1.6°.

The syntheses of Examples 3 and 4 are carried out by the processes shown in Scheme 5:

Scheme 5

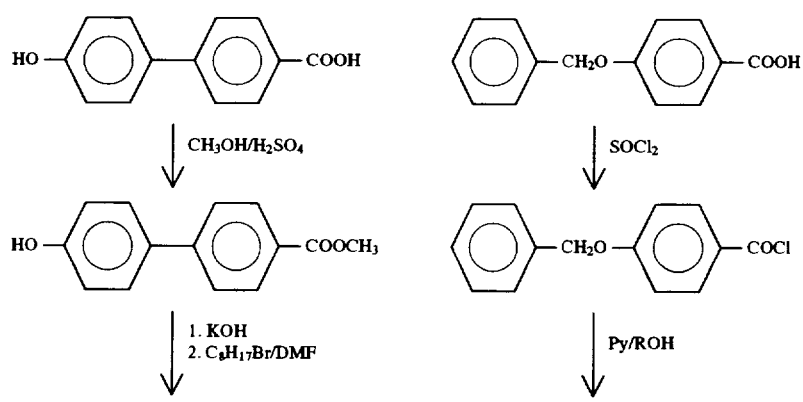

-continued
Scheme 5
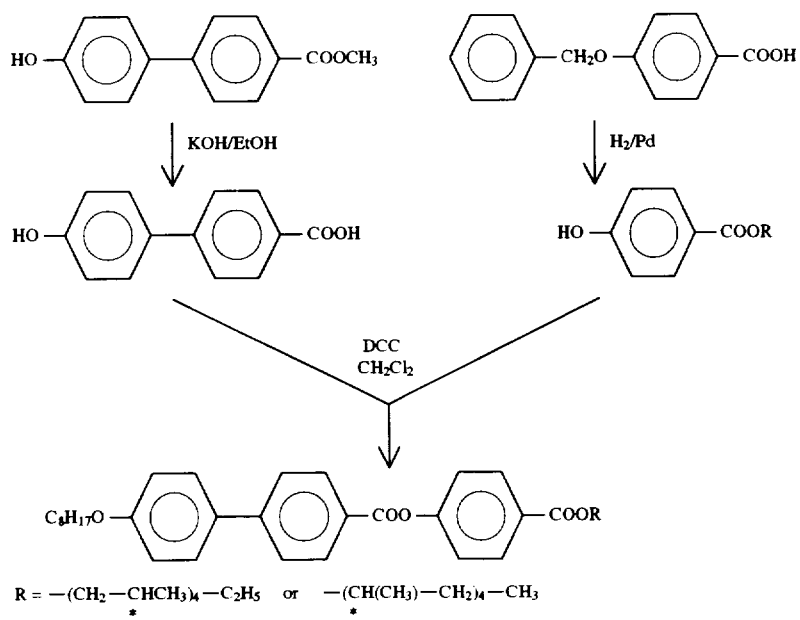
Example 3
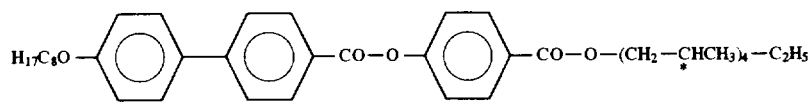
X 54 S$_C$* 116 S$_A$ I. P$_S$ (57° C.): 36 nC/cm$^2$.
Comparative Example 1
Comparative Example 1 was prepared analogously to Example 3, butwith only one methylbranch for the same chain length:
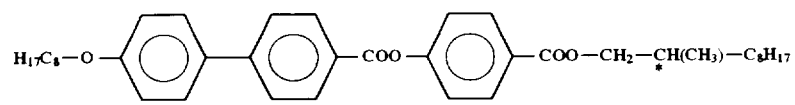
phase range X 66 (S$_3$55) S$_C$ 108 S$_A$ 164I.
Example 4
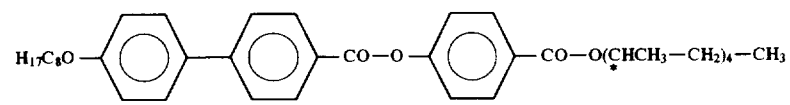
X 54 (S$_3$38) S$_C$* 95 S$_A$ 102 I. P$_S$ (40° C.) : 200 nC/cm$^{-2}$.

Comparative Example 2
Comparative Example 2 was prepared analogously to Example 4, with only one methyl branch for the same chain length:
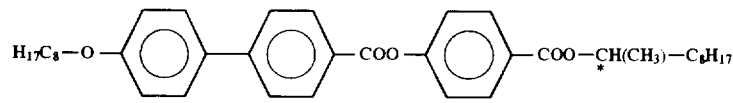
phase range X 63 ($S_{I_A}$ 62.5) $S_{C_A}$ 109 $S_C$ 113 $S_A$ 140I
Syntheses of examples 5, 6 and 7 and of comparative examples 3, 4 and 5:
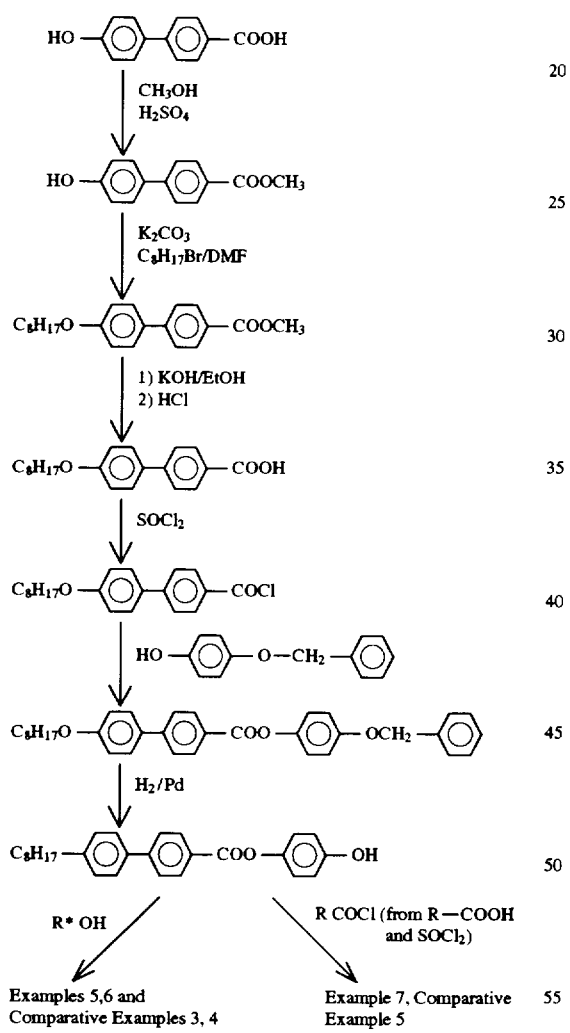

Example 5
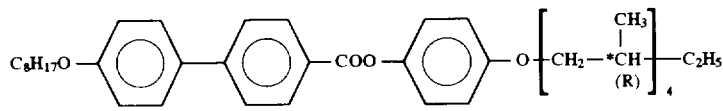
X 55 (S$_4$ 45) S$_3$ 81 S$_C$ 105 S$_A$ 134 I
Comparative Example 3
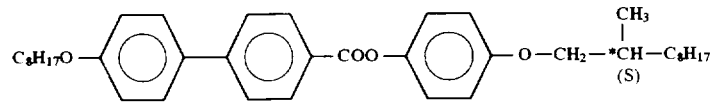
X 84 (S$_4$ 59) S$_3$ 102 S$_C$ 108 S$_A$ 164 I
Example 6
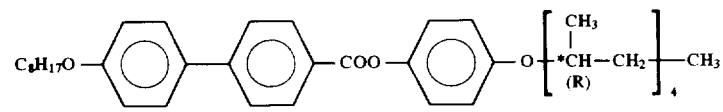
X 42 S$_3$ 50 S$_C$ 90 S$_A$ 116 I
Comparative Example 4
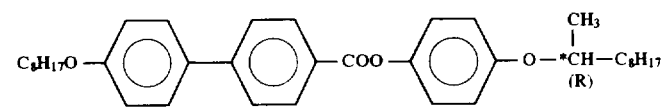
X 65 S$_3$ 81 S$_C$ 95 S$_A$ 144 I
Example 7
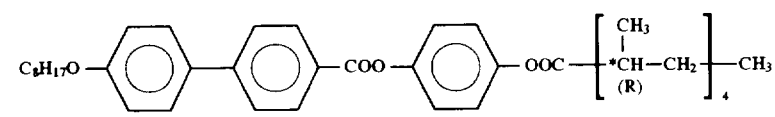
Comparative Example 5
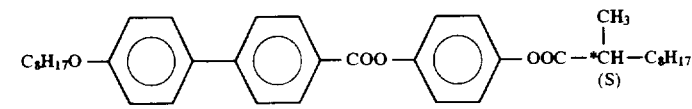
Use Example 1
10% by weight of the substance from Example 1 are dissolved in a test mixture A having the phase sequence S$_C$ 79.5 S$_A$ 90.5 N 102 I.
The phase sequence of the mixture is:
S$_C$ 70 S$_A$ 87 N 95 I The helical twisting power (HTP) in the cholesteric phase is determined as followed, as described in P. Kassubek and G. Meier. Mol. Cryst. Liq. Cryst. 1969, 8, 305:

88° C.: 4.2 μm$^{-1}$
90° C.: 4.8 μm$^{-1}$

Use Example 2

10% by weight of the substance of Example 1 are dissolved in a test mixture A having the phase sequence $S_C$ 79.5 $S_A$ 90.5 N 102 I.

The phase sequence of the mixture is:

$S_C$ 84 $S_A$ 90 N 100 I

The HTP was determined as follows:

91° C.: 3.7 μm$^{-1}$
96° C.: 5.4 μm$^{-1}$

The novel compounds are thus highly suitable for compensating for the pitch in the N* phase, while the phase transitions are only lowered slightly.

A comparison of the spontaneous polarization Ps and the tilt angle 2(–) at $T-T_{S_C \to S_A}$ of example 3 and comparative example 1

| Substance   | $T-T_{S_C \to S_A}$ | $P_S$ [nC/cm$^2$] | 2(–) [°] |
|-------------|---------------------|-------------------|----------|
| Ex. 3       | 9                   | 18                | 25       |
| Ex. 3       | 30                  | 28                | 31.5     |
| Ex. 3       | 50                  | 34.5              | 31       |
| Comp. Ex. 1 | 9                   | 6                 | 14       |
| Comp. Ex. 1 | 30                  | 10                | 19.3     |
| Comp. Ex. 1 | 50                  | 12.5              | 20.4     | shows that the novel compound has significantly higher spontaneous polarization, which results in a faster response speed. In addition, the tilt angle in the novel substance is closer to the ideal value of 45°, i.e. better contrast can be acheived.

A comparison of the spontaneous polarization and tilt angle at $T-T_{S_C \to S_A}$ of example 4 and comparative example 2

| Substance   | $T-T_{S_C \to S_A}$ | $P_S$ [nC/cm$^2$] | 2(–) [°] |
|-------------|---------------------|-------------------|----------|
| Ex. 4       | 3                   | 89                | 25.5     |
| Comp. Ex. 2 | 3                   | 46                | 15       | shows that the novel compound has significantly higher spontaneous polarization and a significantly greater tilt angle.

A comparison of the spontaneous polarization and tilt angle at 6K below the $S_C$–$S_A$ transitiontemperature ofexamples 5 and 6 and comparative examples 3 and 4

| Substance   | $P_S$ [nC/cm$^2$] | 0 (°) |
|-------------|-------------------|-------|
| Ex. 5       | 5,4               | 18,4  |
| Comp. Ex. 3 | 1,9               | 9,5   |
| Ex. 6       | 52,4              | 20,2  |
| Comp. Ex. 4 | 26,6              | 11,7  | shows that the compounds according to the invention have a significantly higher spontaneous polarization and a significantly greater tilt angle.

In addition, examples 5 and 6 have lower melting points and broader $S_C$ phases than the respective comparative examples.

We claim:

1. A compound of the formula (I) with multiple methyl branches,

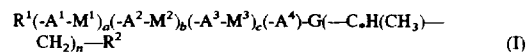

$$R^1(-A^1-M^1)_a(-A^2-M^2)_b(-A^3-M^3)_c(-A^4)-G(-C_*H(CH_3)-CH_2)_n-R^2 \quad (I)$$

in which the symbols and indices have the following meanings:

\* is a chiral carbon atom;

R$^1$ is hydrogen, —CN, —F, —Cl, —CF$_3$, —CHF$_2$, —CH$_2$F, —OCF$_3$, —OCHF$_2$, —OCH$_2$F or a straight-chain or branched alkyl radical having 1 to 20 carbon atoms (with or without an asymmetrical carbon atom), where one or more —CH$_2$— groups may also be replaced by —O—, —S—, —CO—O—, —O—CO—, —O—CO—O—, —CO—, —CS—, —CH=CH—, —C≡C—, cyclopropane-1,2-diyl, —Si(CH$_3$)$_2$—, 1,4-phenylene, trans-1,4-cyclohexylene or trans-1,3-cyclopentylene, with the proviso that oxygen atoms and/or sulfur atoms must not be bonded directly to one another, and/or where one or more H atoms of the alkyl radical may be substituted by —F, —Cl, —Br, —OR$^3$, —SCN, —OCN or —N$_3$, or R$^1$ is alternatively one of the following groups (optically active or racemic):

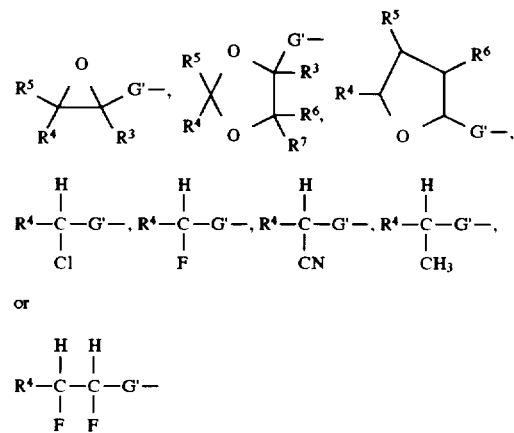

or R$^1$ is a radical of the formula -G-(C$_*$H(CH$_3$)—CH$_2$)$_n$R$^2$;

R$^2$ is an n-alkyl group having 1 to 6 carbon atoms;

G is —CO—O—CH$_2$—, —CO—O—, —O—CO—, —O—CO—O—CH$_2$—, —O—CO—O—, —O—CH$_2$—, —O—, —S— or a single bond;

G' is —CO—O—, —CH$_2$—O— or a single bond;

R$^3$, R$^4$, R$^5$, R$^6$ and R$^7$ are identical or different and are hydrogen or a straight-chain or branched alkyl radical having 1 to 16 carbon atoms (with or without an asymmetrical carbon atom), where one or more —CH$_2$— groups may also be replaced by —O— and/or —CH=CH—, with the proviso that oxygen atoms must not be bonded directly to one another, and/or where one or more H atoms of the alkyl radical may be substituted by —F or —Cl; R$^4$ and R$^5$ together may also be —(CH$_2$)$_4$— or —(CH$_2$)$_5$— if they are bonded to an oxirane, dioxolane or tetrahydrofuran system;

M$^1$, M$^2$, M$^3$ and M$^4$ are identical or different and are —CO—O—, —O—CO—, —O—CO—O—, —CH$_2$—O—, —O—CH$_2$—, —CH$_2$—S—, —S—CH$_2$—, —CH=CH— or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or $CH_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, or naphthalene-2,6-diyl, in which one or more H atoms may be replaced by F, Cl and/or CN;

a, b and c are 0 or 1 and a+b+c is 1, 2 or 3; and n is 2, 3, 4, 5 or 6.

2. A compound as claimed in claim 1, wherein the symbols and indices in the formula (I) have the following meanings:

$R^1$ is hydrogen, or a straight-chain or branched alkyl radical having 1 to 20 carbon atoms (with or without an asymmetrical carbon atom), where one or more —$CH_2$— groups may also be replaced by —O—, —CO—O—, —O—CO—, —O—CO—O—, —CH=CH—, —C≡C—, cyclopropane-1,2-diyl or —Si(CH$_3$)$_2$—, with the proviso that oxygen atoms must not be bonded directly to one another, and/or where one or more H atoms of the alkyl radical may be substituted by —F or —Cl, or $R^1$ is one of the following groups (optically active or racemic):

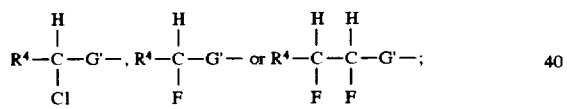

or $R^1$ is a group of formula -G-(C*H(CH$_3$)—CH$_2$)$_n$—$R^2$;

$R^2$ is methyl or ethyl;

G is —CO—O—CH$_2$—, —CO—O—, —O—CO—, —O—CO—O—CH$_2$—, —O—CO—O—, —O—CH$_2$—, —O— or a single bond;

G' is —CO—O—, —CH$_2$—O— or a single bond;

$R^4$ is hydrogen or a straight-chain or branched alkyl radical having 1 to 16 carbon atoms (with or without an asymmetrical carbon atom), where one or more CH$_2$— groups may also be replaced by —O—, with the proviso that oxygen atoms must not be bonded directly to one another, and/or where one or more H atoms of the alkyl radical may be substituted by —F;

$M^1$, $M^2$, $M^3$ and $M^4$ are identical or different and are —CO—O—, —O—CO—, —O—CO—O—, —CH$_2$—O—, —O—CH$_2$—, —C≡C—, —CH$_2$—CH$_2$—CO—O—, —O—CO—CH$_2$—CH$_2$— or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, pyridazine-3,6-diyl, in which one or two H atoms may be replaced by F, pyridine-2,5-diyl, in which one or more H atoms may be replaced by F, pyrimidine-2,5-diyl, in which one or two H atoms may be replaced by F, trans-1,4-cyclohexylene, in which one or two H atoms may be replaced by CN and/or $CH_3$, 1,3,4-thiadiazole-2,5-diyl, 1,3-thiazole-2,4-diyl, in which one H atom may be replaced by F, 1,3-thiazole-2,5-diyl, in which one H atom may be replaced by F, thiophene-2,5-diyl, in which one H atom may be replaced by F, or naphthalene-2,6-diyl, in which one or more H atoms may be replaced by F;

a, b and c are 0 or 1 and a+b+c is 1, 2 or 3; and n is 3 or 4.

3. A compound as claimed in claim 1, wherein the symbols and indices in the formula (I) have the following meanings:

R is hydrogen, or a straight-chain or branched alkyl radical having 1 to 20 carbon atoms (with or without an asymmetrical carbon atom), where one or two CH$_2$— groups may also be replaced by —O—, —CO—O—, —O—CO—, —C≡C—, cyclopropane-1,2-diyl or —Si(CH$_3$)$_2$—, with the proviso that oxygen atoms must not be bonded directly to one another, and/or where one or more H atoms of the alkyl radical may be substituted by —F, or $R^1$ is a group of the formula -G-(C*H(CH$_3$)—CH$_2$)$_n$—$R^2$;

$R^2$ is methyl or ethyl;

G is —CO—O—CH$_2$—, —CO—O—, —O—CO—, —O—CH$_2$—, —O— or a single bond;

$M^1$, $M^2$, $M^3$ and $M^4$ are identical or different and are —CO—O—, —O—CO—, —CH$_2$—O—, —O—CH$_2$—, or a single bond;

$A^1$, $A^2$, $A^3$ and $A^4$ are identical or different and are 1,4-phenylene, in which one or more H atoms may be replaced by F, pyridine-2,5-diyl, in which one H atom may be replaced by F, pyrimidine-2,5-diyl, trans-1,4-cyclohexylene, 1,3,4-thiadiazole-2,5-diyl, 1,3-thiazole-2,4-diyl, 1,3-thiazole-2,5-diyl or naphthalene-2,6-diyl;

a, b and c are 0 or 1 and a+b+c is 1, 2 or 3; and n is 3 or 4.

4. A compound as claimed in claim 1, wherein the symbols and indices in the formula (I) have the following meanings:

$R^1$ is a straight-chain or branched alkyl, alkoxy or ester group having 1 to 16 carbon atoms;

$R^2$ is methyl or ethyl;

G is —CO—O—CH$_2$—, —CO—O—, —O—CO—, —O—CH$_2$— or —O—;

$M^1$, $M^2$, $M^3$ and $M^4$ are identical or different and are —CO—O—, —O—CO—, —CH$_2$—O—, —O—CH$_2$—, or a single bond;

$A^1$, $A^2$, $A^3$ and $A^4$ are identical or different and are 1,4-phenylene, in which one or two H atoms may be replaced by F, pyrimidine-2,5-diyl, pyridine-2,5-diyl, in which one H atom may be replaced by F, trans-1,4-cyclohexylene, 1,3,4-thiadiazole-2,5-diyl or 1,3-thiazole-2,5-diyl;

a, b and c are 0 or 1 and a+b+c is 1, 2 or 3; and n is 3 or 4.

5. A compound as claimed in claim 1, wherein the group (-$A^1$-$M^1$)$_a$(-$A^2$-$M^2$)$_b$(-$A^3$-$M^3$)$_c$(-$A^4$) in the formula (I) has one of the following meanings:

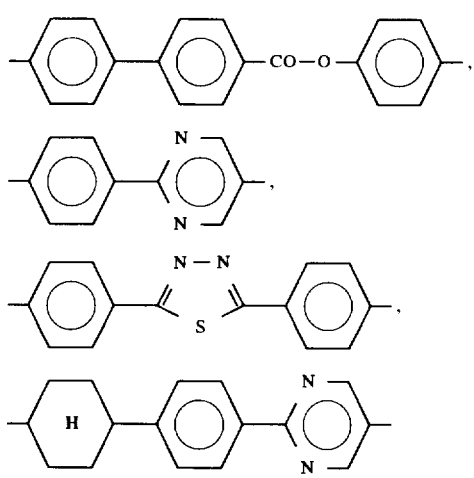

6. A liquid-crystal mixture comprising one or more compounds of the formula (I) as claimed in claim 1.

7. A liquid-crystal mixture as claimed in claim 6, which is ferroelectric.

8. A liquid-crystal mixture as claimed in claim 6, which contains from 0.1 to 60 mol % of from 1 to 5 compounds of the formula (I).

9. A switching and/or display device comprising outer plates, electrodes, at least one polarizer, at least one alignment layer and a liquid-crystalline medium, where the liquid-crystalline medium is a liquid-crystal mixture as claimed in claim 6.

* * * * *